(12) United States Patent
Story

(10) Patent No.: US 11,446,216 B2
(45) Date of Patent: Sep. 20, 2022

(54) RELATION TO THE MANUFACTURE OF PERSONAL CLEANSING COMPOSITIONS

(71) Applicant: THOS. BENTLEY & SON LIMITED, Leeds (GB)

(72) Inventor: John Michael Story, Leeds (GB)

(73) Assignee: THOS. BENTLEY & SON LIMITED, Leeds (GB)

( * ) Notice: Subject to any disclaimer, the term of this patent is extended or adjusted under 35 U.S.C. 154(b) by 0 days.

(21) Appl. No.: 17/268,304

(22) PCT Filed: Aug. 12, 2019

(86) PCT No.: PCT/GB2019/052266
§ 371 (c)(1),
(2) Date: Feb. 12, 2021

(87) PCT Pub. No.: WO2020/035671
PCT Pub. Date: Feb. 20, 2020

(65) Prior Publication Data
US 2021/0236393 A1 Aug. 5, 2021

(30) Foreign Application Priority Data
Aug. 14, 2018 (GB) ..................... 1813273

(51) Int. Cl.
*A61K 8/02* (2006.01)
*A61K 8/06* (2006.01)
*A61K 8/36* (2006.01)
*A61K 8/37* (2006.01)
*A61K 8/46* (2006.01)
*A61K 8/92* (2006.01)

(52) U.S. Cl.
CPC ............ *A61K 8/0216* (2013.01); *A61K 8/062* (2013.01); *A61K 8/361* (2013.01); *A61K 8/375* (2013.01); *A61K 8/466* (2013.01); *A61K 8/922* (2013.01); *A61K 2800/30* (2013.01); *A61K 2800/596* (2013.01); *A61K 2800/75* (2013.01)

(58) Field of Classification Search
CPC ......... C11D 1/04; C11D 17/0047; C11D 1/12; C11D 11/0082; C11D 17/006; C11D 17/06; C11D 1/28; C11D 1/345; C11D 1/83; C11D 1/34; C11D 17/0034; C11D 1/02; C11D 1/123; C11D 1/126; C11D 1/14; C11D 1/667; C11D 1/74; C11D 3/2093; C11D 10/042; C11D 10/045; C11D 13/18; C11D 17/0017; C11D 1/06; C11D 1/10; C11D 1/143; C11D 3/126; C11D 3/2006; C11D 3/2079; C11D 9/26; C11D 10/04; C11D 13/00; C11D 17/00; C11D 1/37; C11D 1/66; A61K 2800/30; A61K 2800/596; A61K 2800/75; A61K 8/0216; A61K 8/062; A61K 8/361; A61K 8/375; A61K 8/466; A61K 8/922; A61K 8/8152; A61K 35/74; A61K 35/747; A61K 2800/10; A61K 2800/48; A61K 8/99; A61K 8/86; A61K 9/0014; A61K 35/744; A61K 8/737; A61K 8/8147; A61K 8/8158; A61K 2035/11; A61K 8/34; A61K 8/347; A61K 2800/28; A61K 2800/52; A61K 2800/548; A61K 8/042; A61K 8/06; A61K 8/31; A61K 8/345; A61K 8/44; A61K 8/463; A61K 8/84; A61K 8/9789; A61K 2800/5426; A61K 31/787; A61K 36/28; A61K 8/91; A61K 2300/00; A61K 2800/262; A61K 2800/5422; A61K 2800/5424; A61K 2800/546; A61K 2800/592; A61K 2800/594; A61K 2800/654; A61K 31/7048; A61K 38/12; A61K 47/32; A61K 8/04; A61K 8/20; A61K 8/24; A61K 8/25; A61K 8/37; A61K 8/41; A61K 8/416; A61K 8/42; A61K 8/4926; A61K 8/4946; A61K 8/602; A61K 8/731; A61K 8/817; A61K 8/8194; A61K 8/927; A61K 9/19; A61K 2800/21;
(Continued)

(56) References Cited

U.S. PATENT DOCUMENTS

| 5,372,751 A | 12/1994 | Rys-Cicciari et al. |
| 6,074,998 A * | 6/2000 | He .................. C11D 3/2093 510/141 |
| 6,458,751 B1 * | 10/2002 | Abbas .................. C11D 1/04 510/156 |
| 6,537,954 B2 | 3/2003 | Schultz et al. |
| 2006/0089279 A1 * | 4/2006 | Brennan ............... A61K 8/466 510/141 |
| 2015/0322388 A1 | 11/2015 | Pan et al. |
| 2017/0172892 A1 * | 6/2017 | Dai .................... A61K 8/39 |

FOREIGN PATENT DOCUMENTS

| EP | 1174494 A1 | 1/2002 |
| GB | 783027 A | 9/1957 |

(Continued)

OTHER PUBLICATIONS

Durasoft Brochure, Stephenson Personal Care, DurosoftTM Naturally differentTM, Naturally Derived Polyglycerol Ester Emulsifiers, published Jul. 2017 at https://glenncorp.com/wp-content/uploads/2017/07/Durosoft-SF_Brochure.pdf (Year: 2017).*

(Continued)

*Primary Examiner* — Audrea B Coniglio
(74) *Attorney, Agent, or Firm* — Innovators Legal

(57) ABSTRACT

The invention relates to a method of making solid cleansing compositions which comprise a non-soap anionic surfactant, a carrier, an emulsifier and water. The method entails preparing an emulsion of the components at an elevated temperature using excess water and subjecting the emulsion to cooling and solidification, wherein the water content is reduced. The invention further relates to the emulsions and to the novel solid cleansing compositions formed therefrom.

28 Claims, No Drawings

(58) Field of Classification Search
CPC .......... A61K 2800/49; A61K 2800/522; A61K
2800/54; A61K 2800/80; A61K 2800/805;
A61K 2800/87; A61K 2800/88; A61K
38/00; A61K 45/06; A61K 8/0208; A61K
8/0241; A61K 8/0245; A61K 8/025;
A61K 8/044; A61K 8/046; A61K 8/19;
A61K 8/29; A61K 8/342; A61K 8/365;
A61K 8/39; A61K 8/442; A61K 8/494;
A61K 8/498; A61K 8/4993; A61K 8/553;
A61K 8/60; A61K 8/64; A61K 8/676;
A61K 8/68; A61K 8/73; A61K 8/8141;
A61K 8/85; A61K 8/87; A61K 8/894;
A61K 8/898; A61K 8/90; A61K 8/925;
A61Q 19/10; A61Q 19/00; A61Q 5/02;
A61Q 5/12; A61Q 5/06; A61Q 15/00;
A61Q 17/005; A61Q 5/00; A61Q 11/00;
A61Q 17/04; A61Q 19/08; A61Q 5/006;
A61Q 17/00; A61Q 19/005; A61Q
19/007; A61Q 19/02; A61Q 19/002;
A61Q 19/004; A61Q 19/04; A61Q 19/06;
A61Q 1/12; A61Q 1/14; A61Q 5/004;
A61Q 5/065; A61Q 5/08; A61Q 5/10;
A61Q 7/00; A61Q 9/02; A61Q 9/04;
A61P 17/00; A61P 31/04; A61P 17/04;
A61P 17/06; A61P 17/16; A61P 37/08;
A61P 17/08; A61P 17/10; A61P 17/14;
A61P 31/00; A61P 31/02; A61P 31/22;
A61P 33/00; A61P 31/10; A61P 17/02;
A61P 29/00; A61P 37/00; A61P 37/06;
A61P 31/18; A61P 43/00; A01N 43/50;
A01N 31/02; A01N 31/08; A01N
2300/00; A01N 43/16; A01N 43/56;
A01N 43/653; A01N 47/24; A01N 31/14;
A01N 37/40; A01N 63/22; A01N 25/10;
A01N 25/28; A01N 31/16; A01N 33/12;
A01N 37/02; A01N 37/10; A01N 37/34;
A01N 43/40; A01N 43/80; A01N 47/30;
A01N 47/44; A01N 59/16; A01N 65/08;
A01N 65/12; A01N 65/18; A01N 65/20;
A01N 65/24; A01N 65/34; A01N 65/40;
A01N 65/44; A01N 39/00; H04B 7/155;
H04B 7/2606; H04B 17/327; H04B
17/382; H04B 17/40; H04B 7/15542;
H04B 7/14
See application file for complete search history.

(56) References Cited

FOREIGN PATENT DOCUMENTS

| JP | 2002-097495 A | 4/2002 |
|---|---|---|
| JP | 2002-525393 A | 8/2002 |
| JP | 2002-526601 A | 8/2002 |
| WO | 1999/010467 A1 | 3/1999 |
| WO | 2010090354 A1 | 8/2010 |
| WO | 2012/175935 A1 | 12/2012 |

OTHER PUBLICATIONS

Pitman, Stephenson Personal Care launches new range of natural ingredients, May 1, 2018, Cosmeticsdesign.com at https://www.cosmeticsdesign/com/Article/2018/05/01/Stephenson-Personal-Care-launches-new-range-of-natural-ingredients (Year: 2018).*
International Application No. PCT/GB2019/052266, International Search Report dated Nov. 11, 2019.
Nassu et al., "Determination of melting point of vegetable oils and fats by differential scanning calorimetry (DSC) technique", Grasas y Aceites, 1999, pp. 16-21, vol. 50, fasc. 1.
Application No. GB1813273.8, Search Report under Section 17(5) dated Feb. 28, 2019.
Japanese Office Action ("Notice of Reasons for Refusal") dated Oct. 26, 2021 in Japanese Patent Application No. 2021-507752.

* cited by examiner

RELATION TO THE MANUFACTURE OF PERSONAL CLEANSING COMPOSITIONS

CROSS-REFERENCE TO RELATED APPLICATIONS

This application is the 35 U.S.C. § 371 national stage application of PCT Application No. PCT/GB2019/052266, filed Aug. 12, 2019, where the POT claims priority to, and the benefit of, United Kingdom application entitled "Improvements in relation to the manufacture of personal cleansing compositions" having serial no. 1813273.8, filed Aug. 14, 2018, both of which are herein incorporated by reference in their entireties.

This invention relates to improvements in relation to the manufacture of personal cleansing compositions in solid form, for example in particulate form, for example as noodles, flakes, pellets or powders, or in consolidated form, for example in block, bar or tablet form. The invention further relates to the solid compositions produced by such manufacture, and to compositions used in such manufacture.

Soap (that is, fatty acid salts) is an inexpensive solid personal cleansing composition. The large scale manufacture of soap is efficient. However soap is not a product which is universally favoured by consumers. The pH of most soaps is about 9-10, whereas the natural pH of skin is about 5.5. Soap is an effective cleanser but is widely considered to be detrimental to skin. For this reason many consumers avoid soap and instead use "cleansing bars" which contain no soap or only a low proportion of soap.

Many cleansing bars (also called "detergent bars" or "syndet bars") contain an isethionate surfactant as a major component. However for reasons associated with the cost of ingredients, or for reasons associated with the manufacture, or both, cleansing bars are typically significantly more expensive than soap bars.

GB 783027 describes a detergent tablet which contains an alkali metal acyl isethionate and further components, which may include up to 25% of alkali metal soap. It is known in the art that care must be taken to avoid reaction between the alkali metal acyl isethionate and the soap. It is stated in the examples that the ingredients are mixed to form a hot pasty mass which can then be milled and plodded. It may be inferred that the alkali metal acyl isethionate and the soap do not react in the hot pasty mass.

It is an object of embodiments of the invention to make a solid cleansing composition by a more efficient and less expensive method.

In accordance with a first aspect of the present invention there is provided a method of making a solid cleansing composition, the composition comprising:
(a) at least 15% wt of a non-soap anionic surfactant having a melting point of at least 45° C.;
(b) at least 10% wt of a carrier having a melting point of at least 45° C.;
(c) at least 1% wt of an emulsifier; and
(d) at least 3% wt water;
wherein the composition is a solid throughout the range from 0° C. to 40° C.;
and wherein the method comprises:
(i) preparing an emulsion containing the components (a) to (d), but with a greater mass of water present than in the solid cleaning composition, the temperature of the emulsion being at least 45° C.,
(ii) subjecting the emulsion to cooling and solidification, wherein its water content is reduced during the cooling and solidification to produce the solid cleansing composition having components (a) to (d) in the amounts defined.

Suitably the solid cleansing composition produced by the method of the first aspect has a completely or predominantly homogeneous microstructure.

Suitably the emulsion formed in step (i) and the solid cleansing composition do not contain soap. Suitably the emulsion formed in step (i) and the solid cleansing composition do not contain starch. Suitably the emulsion formed in step (i) and the solid cleansing composition do not contain soap or starch.

In accordance with a second aspect of the present invention there is provided a solid cleansing composition which comprises:
(a) at least 15% wt of a non-soap anionic surfactant having a melting point of at least 45° C.;
(b) at least 10% wt of a carrier having a melting point of at least 45° C.;
(c) at least 1% wt of an emulsifier; and
(d) at least 3% wt water;
wherein the composition is a solid throughout the range from 0° C. to 40° C.

In accordance with a third aspect of the present invention there is provided a solid cleansing composition which comprises
(a) at least 20% wt and up to 60% wt of a non-soap anionic surfactant having a melting point of at least 45° C.;
(b) at least 20% wt and up to 60% wt of a carrier having a melting point of at least 45° C.;
(c) at least 2% wt and up to 9% wt of an emulsifier;
(d) at least 5% wt and up to 16% wt of water;
and which preferably does not contain soap or starch;
wherein components (a) to (d) make up at least 70% and up to 100% of the weight of the solid cleansing composition;
wherein the composition is a solid throughout the range from 0° C. to 40° C.

Suitably the solid cleansing composition of the second aspect and of the third aspect has a completely or predominantly homogeneous microstructure.

In accordance with a fourth aspect of the present invention there is provided an emulsion for the preparation of a solid cleansing composition, the emulsion comprising
(a) at least 12% wt of a non-soap anionic surfactant having a melting point of at least 45° C.;
(b) at least 8% wt of a carrier having a melting point of at least 45° C.;
(c) at least 1% wt of an emulsifier; and
(d) at least 16% wt water;
wherein the emulsion is at a temperature of at least 45° C.

In accordance with a further aspect of the present invention there is provided a precursor composition for the preparation of a solid cleansing composition, the precursor composition comprising
(a) at least 12% wt of a non-soap anionic surfactant having a melting point of at least 45° C.;
(b) at least 8% wt of a carrier having a melting point of at least 45° C.;
(c) at least 1% wt of an emulsifier; and
(d) at least 16% wt water;
wherein the precursor composition is an emulsion at a temperature of at least 45° C.

In accordance with a fifth aspect of the present invention there is provided an emulsion for the preparation of a solid cleansing composition, the emulsion comprising (a) at least 20% wt and up to 50% wt of a non-soap anionic surfactant having a melting point of at least 45° C.;
(b) at least 20% wt and up to 50% wt of a carrier having a melting point of at least 45° C.;
(c) at least 2% wt and up to 9% wt of an emulsifier; and
(d) at least 16% wt water;
wherein the emulsion is at a temperature of at least 45° C., and
wherein components (a) to (d) make up at least 70% and up to 100% of the weight of the emulsion.

The following further definitions apply to all aspects of the invention, whether they be to the method, to the solid cleansing composition or to the emulsion (or precursor composition); unless it should be stated otherwise or the context demands otherwise.

Suitably, in the first, fourth and fifth aspects the emulsion is at a temperature at which it is a free-flowing liquid.

In a preferred feature of the first, fourth or fifth aspect of the invention the non-soap anionic surfactant (a) has a melting point of at least 50° C., the carrier (b) has a melting point of at least 50° C., and the emulsion is at a temperature of at least 50° C., at which temperature the emulsion is a free-flowing liquid.

In a preferred feature of the first, fourth or fifth aspect of the invention the non-soap anionic surfactant (a) has a melting point of at least 55° C., the carrier (b) has a melting point of at least 55° C., and the emulsion is at a temperature of at least 55° C., at which temperature the emulsion is a free-flowing liquid.

In a preferred feature of the first, fourth or fifth aspect of the invention the non-soap anionic surfactant (a) has a melting point of at least 60° C., the carrier (b) has a melting point of at least 60° C., and the emulsion is at a temperature of at least 60° C., at which temperature the emulsion is a free-flowing liquid.

Suitably, in the method of the first aspect the emulsion is cooled and solidified to form particulates, for example noodles, pellets, flakes or powder or the like, which may be consolidated into a mass and separated into blocks, bars, tablets or the like.

Ultimately the product offered to consumers of cleansing bars may be a bar or tablet of conventional size, for example 50-200 g; typically 80-130 g. Alternatively the product could provided in the form of noodles, pellets, particles, flakes, chips or the like from which a manufacturer may make such bars or tablets.

The particulates and the resulting solid consolidated mass are suitably homogeneous in their microstructure, not heterogeneous. In preferred embodiments there is no post-solidification addition of any components to the solid cleansing material; the entire process preferably occurs in the liquid phase.

Preferably in the first aspect, and the fourth and fifth aspects, the emulsion is at a temperature of at least 60° C., preferably at least 70° C., preferably at least 75° C., preferably at least 80° C., preferably at least 85° C.

Preferably in the first aspect, and the fourth and fifth aspects, the emulsion is at a temperature of up to 100° C., preferably up to 95° C., more preferably up to 90° C.

Preferably in the first aspect, and the fourth and fifth aspects, the emulsion is at a temperature in the range 80° C. to 95° C., most preferably in the range 85° C. to 90° C.

Preferably the non-soap anionic surfactant (a) is added to water (d) which is at a selected elevated temperature. The emulsifier (c) is preferably added at the same time as the surfactant (a) or subsequently; the carrier (b) is added to the water after the addition of the surfactant (a) and emulsifier (c). The addition to the water of the emulsifier before the carrier means that the emulsifier is present to immediately start to emulsify the carrier, and preventing it from forming a film which otherwise could disrupt the process.

Other ingredients, if present, are preferably added whenever convenient. Frequently it is suitable to add them to the water with the anionic surfactant, or before.

It is important in the method that the emulsion contains excess water, compared with the water content of the solid cleansing composition. The presence of excess water allows the temperature of the mass to be controlled. Water is typically lost from the emulsion during the cooling and solidification. This may be carried out by using a spray dryer or any other method in which the emulsion is separated into droplets or pellets which are exposed to air and may rapidly lose heat, as they cool.

Preferably the mass of water used for the process of manufacture is at least 30% higher than the mass of water present in solid cleansing composition; preferably at least 40% higher; preferably at least 50% higher; preferably at least 60% higher, and in some preferred embodiments at least 70% higher. In some especially preferred embodiments the mass of water is at least 100% higher than the mass of water in the solid cleansing composition, and may be at least 125% higher.

Preferably the mass of water used for the process of manufacture is not more than 300% higher than the mass of water present in the solid cleansing composition; preferably not more than 250% higher; preferably not more than 200% higher.

It should be noted that the above definitions compare the mass of water used in the process of manufacture—that is, the mass of water in the emulsion—with the mass of water present in the solid cleansing composition. They do not define the mass of water in the emulsion expressed in terms of total mass of components in the emulsion, nor the mass of water in the solid cleansing composition expressed in terms of total mass of components in the solid cleansing composition. Such definitions are given later in this specification.

The manufacture of syndet bars by methods used up to this time has been slow, compared to manufacture of soap bars. This is one reason why syndet bars are expensive, in comparison with soap bars. By virtue of the ingredients and process parameters used the method of the first aspect is essentially able to use the equipment and techniques of conventional soap making, leading to significantly higher production rates that have been achieved before for syndet bars.

Suitably component (a) may comprise a sulfate, sulfonate, amphoacetate, sulfoacetate, sulfosuccinate, phosphate or carboxylate non-soap anionic surfactant; selected in each case to have a melting point of at least 45° C.

Suitably component (a) may have a melting point of at least 50° C., preferably of at least 55° C., more preferably of at least 60° C. In some preferred embodiments component (a) has a melting point of at least 65° C.

Sulfate non-soap anionic surfactants may include ammonium lauryl sulfate, sodium lauryl sulfate (SLS), fatty alcohol sulfates, and alkyl-ether sulfates, for example sodium laureth sulfate (SLES), sodium myreth sulfate and polyoxyethylene fatty alcohol ether sulfates.

Sulfonate non-soap anionic surfactants may include alkyl sulfonates, alkylbenzene sulfonates, alkenyl sulfonates, alkyl succinate sulfonates, alkylphenol sulfonates perflouoralkylsulfonates and acyl isethionates. A suitable alkyl succinate sulfonate is disodium laureth sulfosuccinate.

Amphoacetates, sulfoacetates, and sulfosuccinates non-soap anionic surfactants may include sodium lauryl sulfoacetate and disodium laureth sulfosuccinate.

Phosphate non-soap anionic surfactants may include alkyl-aryl ether phosphates and alkyl ether phosphates.

Carboxylate non-soap anionic surfactants may include sarcosinates, for example sodium lauroyl sarcosinate, and carboxylate-based fluorosurfactants, for example perfluorononanoate and perfluorooctanoate (PFOA or PFO).

Preferred non-soap anionic surfactants (a) for use on this invention are acyl isethionates.

An acyl isethionate for use in this invention is suitably of formula

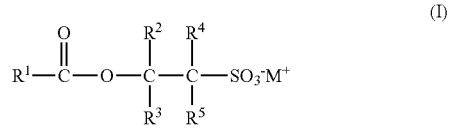

(I)

wherein $R^1$ is an alkyl or alkenyl group having from 8 to 24 carbon atoms;
$R^2$ is a hydrogen atom or an alkyl or alkenyl group having from 1 to 8 carbon atoms;
$R^3$ is a hydrogen atom or an alkyl or alkenyl group having from 1 to 8 carbon atoms;
$R^4$ is a hydrogen atom or an alkyl or alkenyl group having from 1 to 8 carbon atoms;
$R^5$ is a hydrogen atom or an alkyl or alkenyl group having from 1 to 8 carbon atoms;
and $M^+$ is a cation.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations (it should be noted here that when $M^+$ represents an alkaline earth metal cation $M^+$ has a double positive charge and the compound has two anions). Preferably $M^+$ represents a potassium cation, or, especially, a sodium cation.

$R^1$ may be an alkyl group or an alkenyl group. Preferably $R^1$ is an alkyl group. In some embodiments component (a) may comprise a surfactant derived from a mixture of fatty acids to form a mixture of compounds of formula (I) in which $R^1$ may be different.

$R^1$ is preferably the residue of a fatty acid. Fatty acids obtained from natural oils often include mixtures of fatty acids. For example the fatty acid obtained from coconut oil contains a mixture of fatty acids including C12 lauric acid, C14 myristic acid, C16 palmitic acid, C8 caprylic acid, and C18 stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behenic acid, erucic acid, docosa-hexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil, in which lauric acid chains predominate.

$R^2$ is preferably a hydrogen atom or an alkyl or alkenyl group having from 1 to 4 carbon atoms. Most preferably $R^2$ is a hydrogen atom.

$R^3$ is preferably a hydrogen atom or an alkyl or alkenyl group having from 1 to 4 carbon atoms. Most preferably $R^3$ is a hydrogen atom.

$R^4$ is preferably a hydrogen atom or an alkyl or alkenyl group having from 1 to 4 carbon atoms. Most preferably $R^2$ is a hydrogen atom.

$R^6$ is preferably a hydrogen atom or an alkyl or alkenyl group having from 1 to 4 carbon atoms. Most preferably $R^2$ is a hydrogen atom.

In some embodiments three of the entities $R^2$, $R^3$, $R^4$ and $R^5$ are hydrogen and only one is an alkyl or alkenyl group having from 1 to 8 carbon atoms. In such embodiments preferably $R^3$, $R^4$ and $R^5$ are hydrogen and $R^2$ is the alkyl or alkenyl group.

However in especially preferred embodiments $R^2$, $R^3$, $R^4$ and $R^5$ are all hydrogen.

In some especially favoured embodiments component (a) comprises one or more or all of sodium lauroyl isethionate (SLI), sodium oleoyl isethionate and sodium cocoyl isethionate (SCI), which is closely related to but not identical to SLI.

Most preferably the component (a) of the composition of the present invention comprises or consists of sodium cocoyl isethionate and/or sodium lauroyl isethionate.

An acyl isethionate may serve as the only constituent of component (a). However in some acceptable embodiments component (a) may comprise an acyl isethionate in admixture with one or more further non-soap anionic surfactants, for example any of those defined above. In such admixture embodiments acyl isethionate(s) suitably constitute(s) at least 50% wt of, and preferably at least 65% wt, of component (a).

Suitably the non-soap anionic surfactant constitutes at least 20% wt of the solid cleansing composition.

Suitably in some embodiments the non-soap anionic surfactant constitutes at least 24% wt of the solid cleansing composition.

Suitably in some embodiments the non-soap anionic surfactant constitutes at least 28% wt of the solid cleansing composition.

Suitably in some embodiments the non-soap anionic surfactant constitutes at least 32% wt of the solid cleansing composition.

Suitably in some embodiments the non-soap anionic surfactant constitutes at least 35% wt of the solid cleansing composition.

Suitably in some embodiments the non-soap anionic surfactant constitutes up to 60% wt of the solid cleansing composition.

Suitably the non-soap anionic surfactant constitutes up to 55% wt of the solid cleansing composition.

Suitably the non-soap anionic surfactant constitutes up to 50% wt of the solid cleansing composition.

Suitably in some embodiments the non-soap anionic surfactant constitutes up to 45% wt of the solid cleansing composition.

Suitably the non-soap anionic surfactant constitutes at least 15% wt of the emulsion.

Suitably in some embodiments the non-soap anionic surfactant constitutes at least 18% wt of the emulsion.

Suitably in some embodiments the non-soap anionic surfactant constitutes at least 22% wt of the emulsion.

Suitably in some embodiments the non-soap anionic surfactant constitutes at least 24% wt of the emulsion.

Suitably in some embodiments the non-soap anionic surfactant constitutes at least 26% wt of the emulsion.

Suitably in some embodiments the non-soap anionic surfactant constitutes up to 50% wt of the emulsion.

Suitably the non-soap anionic surfactant constitutes up to 40% wt of the emulsion.

Suitably the non-soap anionic surfactant constitutes up to 36% wt of the emulsion.

Suitably in some embodiments the non-soap anionic surfactant constitutes up to 32% wt of the emulsion.

Suitably component (b) may have a melting point of at least 50° C., preferably of at least 55° C., more preferably of at least 60° C. In some preferred embodiments component (b) may have a melting point of at least 65° C.

Suitably the carrier, component (b), is selected from a triglyceride, a fatty acid, a fatty alcohol or a wax (including a mixture of any of these components).

Suitably the carrier, component (b), may be beeswax, or may be a triglyceride, fatty acid, fatty alcohol or a wax of vegetal origin.

Preferably component (b) is a triglyceride whose fatty acid chains are residues of a $C_8$ fatty acid, or of higher fatty acids. Preferably they are residues of $C_8$-$C_{32}$ fatty acids, preferably of $C_{10}$-$C_{24}$ fatty acids, preferably of $C_{12}$-$C_{20}$ fatty acids and most preferably of $C_{12-16}$ fatty acids.

Preferably component (b) is a saturated triglyceride. Preferably substantially all fatty acid chains in the triglyceride are saturated. Preferably it is a hydrogenated triglyceride.

Suitably component (b) comprises at least one of hydrogenated rapeseed oil, hydrogenated soybean oil, hydrogenated sunflower oil, hydrogenated palm oil, hydrogenated castor oil, hydrogenated safflower oil and hydrogenated peanut oil. Such oils may be employed singly or in admixture of two, three, four or more or all of these hydrogenated oils. Suitably these oils (summated if more than one is used) make up at least 50% wt, preferably at least 60% wt, preferably at least 70% wt, preferably at least 80% wt, preferably at least 90% wt, and preferably 100% wt, of the carrier, component (b).

Suitable carriers also include fatty acids, suitably $C_8$ fatty acid, or higher fatty acids; for example $C_8$-$C_{32}$ fatty acids, preferably $C_{10}$-$C_{24}$ fatty acids, preferably $C_{12}$-$C_{20}$ fatty acids and most preferably $C_{12}$-$C_{16}$ fatty acids.

Suitable carriers also include fatty alcohols, suitably $C_{16}$ fatty alcohol, or higher fatty alcohol; for example $C_8$-$C_{32}$ fatty alcohols, preferably $C_{10}$-$C_{24}$ fatty alcohols, preferably $C_{12}$-$C_{20}$ fatty alcohols and most preferably $C_{16}$-$C_{18}$ fatty alcohols.

A fatty acid or fatty alcohol residue $C_{xx}$ herein denotes a fatty acid or fatty alcohol residue in which $C_{xx}$ represents the mean of the residues or in which residues $C_{xx}$ constitute more than half the weight of total fatty acid or fatty alcohol residues. If either of these definitions is satisfied the definitions given herein apply.

Suitable waxes include waxes of vegetal origin, for example carnauba wax, and beeswax.

Suitably the carrier, component (b), constitutes at least 15% wt of the solid cleansing composition.

Suitably in some embodiments the carrier constitutes at least 20% wt of the solid cleansing composition.

Suitably in some embodiments the carrier constitutes at least 25% wt of the solid cleansing composition.

Suitably in some embodiments the carrier constitutes at least 30% wt of the solid cleansing composition.

Suitably the carrier constitutes up to 50% wt of the solid cleansing composition.

Suitably the carrier constitutes up to 45% wt of the solid cleansing composition.

Suitably the carrier constitutes up to 40% wt of the solid cleansing composition.

Suitably in some embodiments the carrier constitutes at least 12% wt of the emulsion.

Suitably in some embodiments the carrier constitutes at least 20% wt of the emulsion.

Suitably in some embodiments the carrier constitutes at least 24% wt of the emulsion.

Suitably the carrier constitutes up to 45% wt of the emulsion.

Suitably the carrier constitutes up to 40% wt of the emulsion.

Suitably the carrier constitutes up to 36% wt of the emulsion.

Suitably the carrier constitutes up to 32% wt of the emulsion.

Suitably the % wt of the non-soap anionic surfactant (a) exceeds the % wt of the carrier (b) in the solid cleansing composition.

Suitably the emulsifier, component (c), has an HLB value of at least 6, preferably at least 7, and most preferably at least 8.

Suitably the emulsifier has an HLB value of up to 12, preferably up to 11, and most preferably up to 10.

Thus a suitable range for the emulsifier is from 6 to 12, and a preferred range is from 8 to 10.

The desired HLB value may be that of a single emulsifier or may be achieved by selection of two or more emulsifiers which in combination—calculated as a weighted average taking into account their individual HLB values and their amounts in the blend—achieve the desired HLB value, within the preferred range 6 to 12 or 8 to 10. Thus, a weighted average for emulsifiers $A^1$, $A^2$, $A^3$ . . . can be calculated using the equation:

$$\frac{(\text{mass of } A^1 \times HLB \text{ of } A^1) + (\text{mass of } A^2 \times HLB \text{ of } A^2) + (\text{mass of } A^3 \times HLB \text{ of } A^3) + \ldots}{\text{mass of } A^1 + \text{mass of } A^2 + \text{mass of } A^3 + \ldots}$$

Suitable emulsifiers (c) include sorbitan fatty acid esters and ethoxylated sorbitan fatty acid esters. Suitable sorbitan fatty acid esters, non-ethoxylated, include sorbitan monolaurate, sorbitan monooleate, sorbitan monopalmitate, sorbitan monostearate and sorbitan tristearate. Suitable ethoxylated sorbitan fatty acid esters include polyoxyethylene sorbitan monolaurate, polyoxyethylenesorbitan monooleate, polyoxyethylene sorbitan monopalmitate, polyoxyethylene sorbitan monostearate and polyoxyethylene sorbitan tristearate.

Suitable emulsifiers (c) include glycerol esters of fatty acids; that is, esters of fatty acids and glycerol or polyglycerol. A very wide range of suitable glycerol esters may be made by reaction of glycerol or polyglycerol and $C_6$-$C_{36}$ fatty acids, for example $C_{12}$-$C_{24}$ fatty acids. The fatty acids may be supplied to the esterification reaction as fatty acids or as precursor ester compounds, for example triglycerides. Examples suitable for use in this invention include glycerol monostearate, glycerol monooleate, glycerol palmitate and glycerol monolaurate.

It has been found useful to employ a blend of a glycerol ester of a fatty acid and a sorbitan fatty acid ester or a polyethoxylated sorbitan fatty acid ester, in order to achieve (as a weighted average) an HLB value as defined above for the emulsifier (c).

We have found that one particular sub-class of glycerol esters, described below, is especially beneficial in the present invention.

In such embodiments of the invention the emulsifier, component (c), may be the esterification reaction product of A) a triglyceride, or a fatty acid, or a methyl ester of a fatty acid (or any combination thereof) and B) a polyhydric alcohol which comprises B1) a polyglycerol having at least 3 glycerol units, and B2) glycerol and/or diglycerol.

Preferably the triglyceride A) is an oil (being a liquid at ambient temperature of 18° C.) of plant origin. Preferably it is a naturally-occurring oil, or fat, whose structure has not been chemically modified prior to the esterification reaction.

Batches of triglycerides may vary in their average molecular weight and in their distribution of components but the values stated in this specification define typical situations.

The triglyceride, or the parent triglyceride of the fatty acid or methyl ester of a fatty acid, may be from a single triglyceride source, for example a single named oil or fat, or from a plurality of triglyceride sources, blended.

The fatty acid moieties of the triglyceride, or of the fatty acid or of the methyl ester of a fatty acid, each have an R—CO— moiety, where R represents a hydrocarbyl moiety. Preferably there are at least 6 carbon atoms in the R—CO— moiety, preferably at least 8 carbon atoms; preferably at least 10 carbon atoms; most preferably at least 12 carbon atoms. Preferably there are up to 36 carbon atoms in the R—CO— moiety, preferably up to 28 carbon atoms, preferably up to 24 carbon atoms, more preferably up to 20 carbon atoms.

Suitably fats or oils for use in the esterification reaction may be selected from one or more of the following: almond oil, babassu oil, borage oil, canola oil, cocoa butter, coconut oil, corn oil (maize oil), cottonseed oil, flaxseed oil, grape seed oil, hazelnut oil, illipe, oat oil, olive oil, palm oil, palm olein, palm kernel oil, peanut oil, rapeseed oil, safflower oil, sesame oil, shea nut, soybean oil, tucum oil, sunflower oil, walnut oil, apricot oil, sweet almond oil, avocado oil, baobab oil, blueberry seed oil, calendula oil, camellia oil, cherry kernel oil, cranberry seed oil, hemp oil, jojoba oil, kukur nut oil, macadamia nut oil, manketti oil, melon seed oil, moringe oil, peach kernel oil, pistachio oil, raspberry seed oil, rice bran oil, rosehip oil, soya oil, wheatgerm oil, yangu oil; and their hydrogenated derivatives. A blend of oils or fats may be employed.

Fatty acids or methyl esters of fatty acids, which may be used in the esterification reaction, may include fatty acids or methyl esters derived from any of the fats or oils described above.

Fatty acids which may be used in the esterification reaction, or which may be regarded as 'delivered' to the esterification reaction by a fat or oil, may be selected from one or more of the following: caproic acid, caprylic acid, capric acid, lauric acid, myristic acid, palmitic acid, palmitoleic acid, stearic acid, oleic acid, ricinoleic acid, vaccenic acid, linoleic acid, alpha-linolenic acid (ALA), gamma-linolenic acid (GLA), arachidic acid, gadoleic acid, arachidonic acid (AA), EPA (5,8,11,14,17-eicosapentaenoic acid), behenic acid, erucic acid, DHA (4,7,10,13,16,19-docosahexaenoic acid), and lignoceric acid; and methyl esters of such acids. A blend of fatty acids and/or fatty acid methyl esters may be employed.

Especially preferred acids include caproic acid, caprylic acid, capric acid, lauric acid, myristic acid, palmitic acid, stearic acid, linoleic acid, alpha-linolenic acid (ALA)—and gamma-linoleic acid (GLA). Especially preferred methyl esters may be methyl esters of such fatty acids. Oils or fats which yield such fatty acids are preferred oils or fats. Especially preferred oils are flax seed (flax) oil (which can yield alpha-linolenic acid, ALA), borage seed (borage) oil (which can yield gamma-linolenic acid, GLA) and palm kernel oil (which can yield palmitic acid).

The fatty acid moieties, whether as free acids or methyl esters thereof or as components of a triglyceride, may be saturated or unsaturated. If unsaturated they may suitably have from 1 to 6 double bonds, preferably 1 to 3 double bonds. The fatty acids or methyl esters or parent oils or fats may have been hydrogenated.

In one embodiment the fatty acid moieties, whether free acids or methyl esters thereof or as a component of a triglyceride, are saturated fatty acid moieties having an average molecular weight of less than 282 g/mol, preferably less than 260 g/mol, preferably less than 240 g/mol.

In one embodiment the fatty acid moieties, whether free acids or methyl esters thereof or as a component of a triglyceride, are unsaturated fatty acid moieties having an average molecular weight of less than 320 g/mol, preferably less than 300 g/mol.

Batches of polyglycerols may vary in their average molecular weight and in their distribution of components but the values stated in this specification define typical situations or typical average values.

Preferably the polyglycerol component B1) comprises polyglycerol-4.

Polyglycerol-4 is a commercially available product sold under that name. Polyglycerol-4 is a distribution of a polyglycerol compounds in which the average molecular weight of the polyglycerol is centred on polyglycerol-4.

Preferably the polyglycerol component B1) constitutes at least 50% wt of polyglycerol compounds composed of 3 to 6 glycerol units, preferably at least 60% wt, preferably at least 70% wt, most preferably at least 85% wt.

Preferably the polyglycerol component B1) constitutes at least 20% wt of the compound tetraglycerol, preferably at least 25% wt.

Triglycerol may also be a significant component, even when the average molecular weight of the polyglycerol is centred on polyglycerol-4. Preferably the polyglycerol component B1) constitutes at least 20% wt of the compound triglycerol, preferably at least 25% wt.

Preferably the compound tetraglycerol is present in the polyglycerol component B1) in a higher amount by weight than the compound pentaglycerol.

In some embodiments, the compound tetraglycerol may be the single compound present in the largest proportion by weight in the polyglycerol component B1).

In commercial sources of polyglycerol-4, which may be used in the present invention as a preferred component B1), the proportions by weight of compounds is typically as follows:

triglycerol, 20-50% wt
tetraglycerol, 20-50% wt
higher polyglycerols, 15-40% wt in total other compounds, not more than 20% wt, typically less than 12% wt.

Higher polyglycerols herein means polyglycerol compounds formed of 5 or more glycerol units.

The other compounds may include water and diglycerol. Small amounts of glycerol may sometimes be present.

When glycerol and/or diglycerol is/are present in the polyglycerol source they may supply some or all of the component B2). However the amount of glycerol and diglycerol in a polyglycerol source is generally low. Therefore, in such embodiments, it is generally required to supply glycerol and/or diglycerol to reach the desired amount. This may be done by simple addition of glycerol and/or diglycerol. When a triglyceride is used it may occur by the liberation of glycerol in the esterification reaction.

Preferably the average molecular weight of the polyglycerols in component B1), having at least 3 glycerol units, is in the range 220-500 g/mol, preferably 230-450 g/mol, preferably 240-420 g/mol, preferably 250-400 g/mol, preferably, preferably 260-370 g/mol, 280-350 g/mol, most preferably 300-330 g/mol.

Preferably glycerol constitutes at least 60% wt of the component B2), preferably at least 70% wt, preferably at least 80% wt.

Preferably the ratio by weight of the component B2) to component B1) is one part B2) to at least 4 parts B1), preferably one part B2) to at least 6 parts B1), and most preferably at least one part B2) to at least 8 parts B1).

Preferably the ratio by weight of the component B2) to component B1) is one part B2) to up to 24 parts B1), preferably one part B2) to up to 20 parts B1), and most preferably one part B2) to up to 16 parts B1).

Preferably the components B1) and B2) make up at least 50% wt of the functional fluid, preferably at least 60% wt, preferably at least 70% wt, preferably at least 80% wt, preferably at least 90% wt.

When a triglyceride A) is employed to make component (c) the reaction may be regarded as an interesterification reaction. As noted above glycerol liberated in the reaction may provide some or all of component B2). Preferably it provides all of the glycerol comprised by component B2). Glycerol could be removed or added. Preferably, no glycerol is removed. Preferably, when a triglyceride is used, no glycerol is added.

When a fatty acid or fatty acid methyl ester is used for the esterification reaction to make component (c), component B2) is added to the reaction mixture, suitably in such an amount as to satisfy at least one of the B1):B2) definitions given above.

When a triglyceride is used, preferably the molar ratio of the polyglycerol to the triglyceride in the reaction mixture, based on average molecular weights, is 0.5-5 to 1, preferably 1-4 to 1, preferably 1.5-3 to 1, most preferably 2-2.5 to 1. Average molecular weight may be determined by normal measures. In the case of the triglyceride this may be from GC results. In the case of polyglycerol the raw material specifications may be used.

When a fatty acid or derivative is used, the molar ratio of the polyglycerol to the fatty acid in the reaction mixture, based on average molecular weights, is 0.2-3 to 1, preferably 0.3-2 to 1, preferably 0.5-1.5 to 1, most preferably 0.7-1.3 to 1.

"Esterification" herein includes transesterification or interesterification.

Standard esterification conditions may be used for the manufacture of the glycerol ester emulsifier. Suitably reactions which employ triglycerides are carried out under alkaline conditions (e.g. by addition of sodium hydroxide or potassium hydroxide) and at elevated temperature, for example at least 150° C., preferably 200-250° C. Suitably reactions which employ fatty acids added to the reaction mixture are carried out under acidic conditions (e.g. by addition of sulphonic acid or orthophosphoric acid) and at elevated temperature, for example at least 150° C., preferably 200-250° C.

Preferably the process is a one-pot process, even when it employs a triglyceride.

Preferably the emulsifier is the product of the esterification reaction, without work up (other than neutralisation of any catalyst present). Preferably it is a liquid at ambient temperature of 18° C.

Preferably the emulsifier comprises a plurality of esters, formed from the range of triglycerides present in oil or fat (or from the range of fatty or methyl esters obtained from such triglycerides), and the range of polyglycerol compounds present in an as-supplied "polyglycerol" source. The emulsifier may comprise many esters, for example over 20 ester compounds, or over 50 ester compounds, or over 100 ester compounds. Suitably the emulsifier comprises monoglycerol fatty acid esters, triglycerol fatty acid esters and tetraglycerol fatty acid esters, suitably according to the amounts of the different glycerol and polyglycerol components used in the esterification reaction.

By use of the methods described herein, emulsifiers having an HLB value in the ranges stated above, or able to provide a weighted average HLB value when mixed with other emulsifiers, may be made and are found to be suitably for use in the present invention.

Suitably the emulsion is an oil-in-water emulsion.

The emulsion may be prepared according to the methods disclosed in WO2014170641.

Suitably the emulsifier, component (c), constitutes at least 2% wt of the solid cleansing composition.

Suitably the emulsifier constitutes at least 3% wt of the solid cleansing composition.

Suitably the emulsifier constitutes at least 4% wt of the solid cleansing composition.

Suitably the emulsifier constitutes at least 5% wt of the solid cleansing composition.

Suitably the emulsifier constitutes at least 6% wt of the solid cleansing composition.

The emulsifier may in some embodiments constitute up to 9% wt of the solid cleansing composition.

The emulsifier may in some embodiments constitute up to 8% wt of the solid cleansing composition.

The emulsifier may in some embodiments constitute up to 7% wt of the solid cleansing composition.

The emulsifier may in some embodiments constitute up to 6% wt of the solid cleansing composition.

Suitably the emulsifier, component (c), constitutes at least 2% wt of the emulsion.

Suitably the emulsifier, component (c), constitutes at least 3% wt of the emulsion.

Suitably the emulsifier constitutes at least 4% wt of the emulsion.

Suitably the emulsifier constitutes at least 5% wt of the emulsion.

Suitably in some embodiments the emulsifier constitutes at least 6% wt of the emulsion.

In some embodiments the emulsifier constitutes up to 9% wt of the emulsion.

In some embodiments the emulsifier constitutes up to 8% wt of the emulsion.

In some embodiments the emulsifier constitutes up to 7% wt of the emulsion.

In some embodiments the emulsifier constitutes up to 6% wt of the emulsion.

Suitably the emulsifier constitutes up to 5% wt of the emulsion.

Suitably water, component (d), constitutes at least 5% wt of the solid cleansing composition.

Suitably water constitutes at least 6% wt of the solid cleansing composition.

Suitably water constitutes at least 7% wt of the solid cleansing composition.

Suitably water constitutes at least 8% wt of the solid cleansing composition.

Suitably water constitutes at least 9% wt of the solid cleansing composition.

Suitably water constitutes up to 16% wt of the solid cleansing composition.

Suitably water constitutes up to 14% wt of the solid cleansing composition.

Suitably water constitutes up to 12% wt of the solid cleansing composition.

Suitably water constitutes up to 11% wt of the solid cleansing composition.

Suitably water constitutes up to 10% wt of the solid cleansing composition.

Suitably water, component (d), constitutes at least 12% wt of the emulsion.

Suitably water constitutes at least 16% wt of the emulsion.
Suitably water constitutes at least 20% wt of the emulsion.
Suitably water constitutes at least 22% wt of the emulsion.
Suitably water constitutes at least 24% wt of the emulsion.
Suitably water constitutes up to 50% wt of the emulsion.
Suitably water constitutes up to 40% wt of the emulsion.
Suitably water constitutes up to 36% wt of the emulsion.
Suitably water constitutes up to 32% wt of the emulsion.
Suitably water constitutes up to 30% wt of the emulsion.

Further Components

Optional further components may include (without limitation) polyhydric alcohols, chelants, fatty alcohols and amphoteric surfactants. Further components may offer manufacturing benefits, for example foam control during manufacture, and/or end product user benefits, for example foam control during washing, or emolliency. Further components may preferably be present in total in an amount of up to 30% wt of the solid cleansing composition.

Suitable polyhydric alcohols include $C_2$-$C_4$ alcohols, especially glycols and glycerols, for example monopropylene glycol and glycerine. Polyhydric alcohols, when present, may suitably be present in total in an amount of up to 15% wt of the solid cleansing composition, preferably up to 10% wt.

Suitable chelants include DTPA (diethylenetriaminepentaacetic acid), HEDP (hydroxyethylidene diphosphonic acid), NTA (nitrilotriacetic acid), EDTA (ethylenediaminetetraacetic acid), EDDS (ethylenediamine-N,N'-disuccinic acid), GLDA (N,N-dicarboxymethyl glutamic acid tetrasodium salt) and PDTA (propylenedinitrilotetraacetic acid); and chelants which are analogues of any of the foregoing. Chelants, when present, may suitably be present in total in an amount of up to 0.5% wt of the solid cleansing composition, preferably up to 0.2% wt.

Amphoteric surfactants include betaines, for example cocamidopropyl betaine (CAPB). Amphoteric surfactants, when present, may suitably be present in total in an amount of up to 10% wt of the solid cleansing composition, preferably up to 6% wt.

Preferably a solid cleansing composition of the present invention does not contain any soap (salt of a fatty acid).

Preferably a solid cleansing composition of the present invention does not contain any starch.

The pH of the solid cleansing composition of the present invention (measured at 5 wt % dilution into water) is preferably less than 8, more preferably less than 7, more preferably less than 6.5. Suitably the pH (20%) of the solid cleansing composition is greater than 4, and preferably greater than 5, and preferably greater than 5.5.

In a preferred method of the first aspect the solid composition comprises:
(a) at least 20% wt and up to 60% wt, preferably at least 30% wt and up to 50% wt, of a non-soap anionic surfactant having a melting point of at least 45° C.;
(b) at least 20% wt and up to 60% wt, preferably at least 30% wt and up to 50% wt, of a carrier having a melting point of at least 60° C.;
(c) at least 2% wt and up to 9% wt, preferably at least 3% wt and up to 8% wt, of an emulsifier;
(d) at least 5% wt and up to 16% wt, preferably at least 8% wt and up to 12% wt, of water;
and preferably does not contain soap or starch;
wherein components (a) to (d) make up at least 70% and up to 100% of the weight of the solid cleansing composition. Any further components, when present, are preferably selected from the further components described above.

In a further preferred method of the first aspect the solid cleansing composition comprises:
(a) at least 30% wt and up to 55% wt, of a non-soap anionic surfactant having a melting point of at least 50° C.;
(b) at least 20% wt and up to 40% wt, of a triglyceride having a melting point of at least 60° C.;
(c) at least 5% wt and up to 9% wt of an emulsifier;
(d) at least 8% wt and up to 12% wt of water;
and preferably does not contain soap or starch;
wherein components (a) to (d) make up 80-100% of the weight of the solid cleansing composition. Any further components, when present, may suitably be selected from the further components described above.

The solid cleansing composition of the first aspect is a solid throughout the range from 0 to 40° C. Preferably it is homogenous; no particulates can be seen when a cut surface is examined under an optically microscope at 100× magnification. The homogenous nature is the result of a molten process for the preparation of the solid cleansing composition.

A solid cleansing composition in bar form, having ingredients as defined above in amounts as defined above, is manufactured by preparing an emulsion of the ingredients, in which the amount of water is higher than in the final solid cleansing composition, cooling and drying it and solidifying it to form a particulate mass, consolidating the particulate mass into a monolithic mass, and separating the monolithic mass into bars.

It will be understood by the skilled reader that components of the compositions of the invention—notably components (a) and (b)—may be derived from natural sources and may contain a distribution of molecules about a mean carbon value. Such components are expected to melt over a temperature range, rather than have a sharp melting point. The melting point definitions defined in this specification refer to the temperatures at which a material is completely melted. The method described in the paper *Determination of melting point of vegetable oils and fats by differential scanning calorimetry (DSC) technique* by Renata Tieko Nassu and Lireny Aparecida Guaraldo Gonçalves, in the Grasas y Aceites Vol. 50. Fase. 1 (1999), 16-22 may be consulted. DSC as described in this paper can be used to determine when a material is completely in the liquid state.

Throughout this specification "% wt" means percentage by weight of the composition which is then being defined.

The invention will now be further described by way of illustration with reference to the following examples.

EXAMPLE 1

The following ingredients were added in the amounts stated in the second column and remained in the final product in the amounts stated in the third column. Addition of the ingredients was in the order stated, starting with water.

| Ingredient | As added % wt | Final product % wt |
|---|---|---|
| Water | 25.0 | 9.5 |
| PUREACT I-78 | 36.1 | 43.4 |
| Glycerine | 3.6 | 4.3 |
| DISSOLVINE GL 47S | 0.2 | 0.12 |
| DUROSOFT PK-SG (emulsifier) | 6.9 | 8.4 |
| Hydrogenated sunflower oil | 28.2 | 34.3 |

DISSOLVINE GL 47S is a Trade Mark of Akzo Nobel of the Netherlands. It is a chelating agent, tetrasodium N, N-bis(carboxylatomethyl)-L-glutamate (GLDA).

PUREACT I-78 is a Trade Mark of Innospec Performance Chemicals, of Ellesmere Port, UK. Its major component is sodium cocoyl isethionate (SCI), 83-89% wt; generally also having <1% wt water, <14% wt coconut fatty acid and 4-7% wt sodium isethionate.

DUROSOFT PK-SG is a Trade Mark of Stephenson Group Limited of Leeds, UK. It is an ester of palm kernel oil and polyglycerol-4 (average Mw=250). DUROSOFT PK-SG has an HLB value of 8.8. A preparation of this product is given in WO2014170641.

The sodium cocoyl isethionate (SCI) and the hydrogenated sunflower oil were melted and added to the water, which was at 90° C. The other ingredients were added in turn (the hydrogenated sunflower oil last) and the mass was worked for about 5 hours, whilst still molten. The emulsion, a readily flowable liquid, was then pumped twice through a needle plate having a 0.5 mm mesh and allowed to solidify as particles. During this phase of the processing, water was lost by evaporation and the water content was thereby reduced to approximately 9.5% wt on weight of the resulting solid cleansing composition. The particles were allowed to cool before being passed to a proprietary plodder. A typical plodder is the Duplex Model M400-2/M400-4 plodder manufactured by Mazzoni S.P.A. of Busto Arsizio, Italy. During plodding the temperature of the solid cleansing composition was maintained between 38° C. and 42° C. The billet produced by plodding, still at 38-42° C., was stamped into bars on chilled dies.

The pH of the solid cleansing composition was 6-7 at 5% dilution, as measured by a commercial pH meter.

The resulting products were of high quality, perfectly suitable for use.

EXAMPLE 2

The following ingredients were added in the amounts stated in the second column and remained in the final product in the amounts stated in the third column. Addition of the ingredients was in the order stated, starting with water and the process parameters described for Example 1 were applied.

| Ingredient | As added % wt | Final product % wt |
|---|---|---|
| Water | 29.5 | 10 |
| Glycerine | 3.2 | 4.1 |
| Pentesodium pentatate (pentasodium DTPA - chelant) | 0.05 | 0.06 |
| DEQUEST 2016 (1-Hydroxy ethylidene-1,1,-diphosphonic acid/HEDP-chelant) | 0.05 | 0.06 |
| PUREACT I-78 | 36.0 | 45.9 |
| DUROSOFT PK-SG (emulsifier) | 3.2 | 4.1 |
| Hydrogenated sunflower oil | 28.0 | 35.7 |

DEQUEST is a Trade Mark of Italmatch Chemicals S.P.A. of Genova, Italy.

Preparation of cleansing tablets was as described in Example 1.

The pH of the solid cleansing composition was 6-7 at 5% dilution, as measured by a commercial pH meter.

EXAMPLE 3

The following ingredients were added in the amounts stated in the second column and remained in the final product in the amounts stated in the third column. Addition of the ingredients was in the order stated, starting with water.

| Ingredient | As added % wt | Final product % wt |
|---|---|---|
| Water | 23.5 | 10 |
| Glycerine | 3.5 | 4.1 |
| Stearic acid | 4.3 | 5.1 |
| PUREACT I-78 | 43.5 | 51.1 |
| DUROSOFT PK-SG (emulsifier) | 2.6 | 3.1 |
| Cocamidopropyl betaine (CAPB) | 4.3 | 5.1 |
| Glyceryl monostearate (GMS) | 4.3 | 5.1 |
| Hydrogenated sunflower oil | 13.9 | 16.4 |

Preparation of cleansing tablets was as described in Example 1.

The pH of the cleansing composition was 6-7 at 5% dilution, as measured by a commercial pH meter.

The resulting tablets were quite soft but still suitable for use.

EXAMPLE 4

The following ingredients were added in the amounts stated in the second column and remained in the final product in the amounts stated in the third column. Addition of the ingredients was in the order stated, starting with water.

| Ingredient | As added % wt | Final product % wt |
|---|---|---|
| Water | 15.6 | 10 |
| Glycerine | 2.6 | 2.8 |
| Monopropylene glycol (MPG) | 6.1 | 6.5 |
| PUREACT I-78 | 34.8 | 37.1 |
| Disodium lauryl sulphosuccinate (DSLSS) | 7.0 | 7.4 |
| DUROSOFT PK-SG (emulsifier) | 3.5 | 3.7 |
| Hydrogenated sunflower oil | 30.4 | 32.5 |

Preparation of cleansing tablets was as described in Example 1.

The pH of the cleansing composition was 6-7 at 5% dilution, as measured by a commercial pH meter.

The resulting tablets were slightly too uneven in their dissolution to be regarded as optimal ("somewhat "gritty", in the terminology used in the art) but were still suitable for use.

EXAMPLE 5

The following ingredients were added in the amounts stated in the second column and remained in the final product in the amounts stated in the third column. Addition of the ingredients was in the order stated, starting with water.

| Ingredient | As added % wt | Final product % wt |
|---|---|---|
| Water | 18.7 | 10 |
| Glycerine | 2.6 | 2.8 |
| Monopropylene glycol (MPG) | 4.3 | 4.7 |
| PUREACT I-78 | 34.2 | 37.9 |
| Disodium lauryl sulphosuccinate (DSLSS) | 6.8 | 7.6 |
| DUROSOFT PK-SG (emulsifier) | 3.4 | 3.8 |
| Glyceryl monostearate (GMS) | 3.0 | 3.3 |
| Hydrogenated sunflower oil | 14.1 | 15.6 |
| C16-C18 linear alcohols (NAFOL 1618) | 12.8 | 14.2 |

NAFOL is a trade mark of Sasol of Sandton, South Africa.

Preparation of cleansing tablets was as described in Example 1.

The pH of the cleansing composition was 6-7 at 5% dilution, as measured by a commercial pH meter.

The resulting tablets were quite soft but still suitable for use.

EXAMPLE 6

The following ingredients were added in the amounts stated in the second column and remained in the final product in the amounts stated in the third column. Addition of the ingredients was in the order stated, starting with water.

| Ingredient | As added % wt | Final product % wt |
|---|---|---|
| Water | 25.5 | 10 |
| Glycerine | 3.4 | 4.1 |
| Diethylenetriamine pentaacetic acid (VERSENEX-chelant) | 0.05 | 0.06 |
| DEQUEST 2016 (chelant) | 0.05 | 0.06 |
| PUREACT I-78 | 40.1 | 48.4 |
| Sorbitan monolaurate (SPAN 20) | 3.4 | 4.1 |
| Hydrogenated sunflower oil | 27.6 | 33.3 |

VERSENEX is a Trade Mark of Dow Chemicals of Auburn, Mich., USA.

SPAN 20 is a Trade Mark of Croda International, of Yorkshire, UK.

SPAN 20 has an HLB value of 8.6.

Preparation of cleansing tablets was as described in Example 1.

The pH (20%) of the cleansing composition was 6-7 at 5% dilution, as measured by a commercial pH meter.

The resulting tablets were of high quality, perfectly suitable for use.

EXAMPLE 7

The following ingredients were added in the amounts stated in the second column and remained in the final product in the amounts stated in the third column. Addition of the ingredients was in the order stated, starting with water.

| Ingredient | As added % wt | Final product % wt |
|---|---|---|
| Water | 25.5 | 10 |
| Glycerine | 3.4 | 4.1 |
| Diethylenetriamine pentaacetic acid (VERSENEX chelant) | 0.05 | 0.06 |
| DEQUEST 2016 (chelant) | 0.05 | 0.06 |
| PUREACT I-78 | 40.1 | 48.3 |
| Glyceryl stearate | 2.1 | 2.5 |
| Polyoxyethylene (20) sorbitan monolaurate (Polysorbate 20) | 1.3 | 1.6 |
| Hydrogenated sunflower oil | 27.6 | 33.3 |

Polysorbate 20 has a HLB value of 16.7. Glyceryl stearate has an HLB value of 3.8. The weighted average of these emulsifiers is calculated by the equation given above as 8.8.

Preparation of cleansing tablets was as described in Example 1 except that during the processing small quantities of water were added to keep the foam down.

The pH (20%) of the cleansing composition was 6-7 at 5% dilution, as measured by a commercial pH meter.

The resulting tablets were softer than we would regard as optimal but still suitable for use.

The invention claimed is:

1. A method of making a solid cleansing composition, the composition comprising:
   a. at least 15% wt of a non-soap anionic surfactant having a melting point of at least 45° C.;
   b. at least 10% wt of a carrier having a melting point of at least 45° C.;
   c. at least 3% wt of an emulsifier; and
   d. at least 7% wt water;
   wherein the composition is a solid throughout the range from 0° C. to 40° C.;
   wherein the composition does not contain soap;
   wherein the carrier (b) is a triglyceride;
   wherein the emulsifier, component (c), has an HLB value of up to 12;
   wherein when two or more emulsifiers are present, the HLB is a weighted average taking into account the individual HLB values and amounts of the two or more emulsifiers; and
   wherein the method comprises:
   (i) preparing an emulsion containing the components (a) to (d), but with a greater mass of water present than in the solid cleaning composition, the temperature of the emulsion being at least 45° C.,
   (ii) subjecting the emulsion to cooling and solidification, wherein the water content is reduced during the cooling and solidification to produce the solid cleansing composition having components (a) to (d) in the amounts defined.

2. The method as claimed in claim 1 wherein the emulsion is cooled and solidified to form particles of the solid cleansing composition.

3. The method as claimed in claim 1 wherein the emulsion at a temperature of at least 45° C. is a free-flowing liquid.

4. The method as claimed in claim 1 wherein the solid cleansing composition is soap-free.

5. The method as claimed in claim 1 wherein the mass of water initially present in the emulsion is at least 40% higher than the mass of water present in the solid cleansing composition.

6. The method as claimed in claim 1 wherein component (a) comprises a sulfate, sulfonate, amphoacetate, sulfoacetate, sulfosuccinate, phosphate or carboxylate non-soap anionic surfactant; selected in each case to have a melting point above 45° C.

7. The method as claimed in claim 1, wherein component (a) comprises an acyl isethionate.

8. The method as claimed in claim 1 wherein the non-soap anionic surfactant constitutes at least 20% wt and up to 60% wt of the solid cleansing composition.

9. The method as claimed in claim 1 wherein the carrier (b) comprises one or more of a wax, a triglyceride, a fatty acid or a fatty alcohol.

10. The method as claimed in claim 1, wherein the carrier (b) comprises a triglyceride of vegetal origin which has been hydrogenated to achieve saturation of substantially all fatty acid chains in the triglyceride, and whose fatty acid chains are residues of $C_8$-$C_{32}$ fatty acids.

11. The method as claimed in claim 10 wherein component (b) comprises at least of one of hydrogenated rapeseed oil, hydrogenated soybean oil, hydrogenated sunflower oil, hydrogenated palm oil, hydrogenated castor oil, hydrogenated safflower oil and hydrogenated peanut oil.

12. The method as claimed in claim 1 wherein the carrier (b) constitutes at least 15% wt and up to 40% wt of the solid cleansing composition.

13. The method as claimed in claim 1 wherein the emulsifier, component (c), has an HLB value of at least 6 and up to 12, wherein when two or more emulsifiers are present, the HLB is a weighted average taking into account the individual HLB values and amounts of the two or more emulsifiers.

14. The method as claimed in claim 1 wherein the emulsifier (c) is selected from sorbitan fatty acid esters, ethoxylated sorbitan fatty acid esters and glycerol or polyglycerol esters of fatty acids.

15. The method as claimed in claim 14 wherein the emulsifier (c) comprises glycerol or polyglycerol esters of $C_8$-$C_{24}$ fatty acids.

16. The method as claimed in claim 15 wherein the emulsifier, component (c), is the esterification reaction product of:
A. a triglyceride, or a fatty acid, or a methyl ester of a fatty acid (or any combination thereof), and
B. a polyhydric alcohol which comprises
  B1) a polyglycerol having at least 3 glycerol units, wherein the average molecular weight of the polyglycerol in component B1), having at least 3 glycerol units, is in the range 220-500 g/mol, and
  B2) glycerol and/or diglycerol.

17. The method as claimed in claim 1 wherein the emulsifier, component (c), constitutes at least 2% wt and up to 9% wt of the solid cleansing composition.

18. The method as claimed in claim 1 wherein water, component (d), constitutes at least 5% wt and up to 16% wt of the solid cleansing composition.

19. The method as claimed in claim 1 wherein the solid cleansing composition comprises:
(a) at least 20% wt and up to 60% wt of a non-soap anionic surfactant having a melting point of at least 45° C.;
(b) at least 20% wt and up to 60% wt of a carrier having a melting point of at least 45° C.;
(c) at least 2% wt and up to 9% wt of an emulsifier;
(d) at least 5% wt and up to 16% wt of water;
wherein components (a) to (d) make up at least 70% and up to 100% of the weight of the solid cleansing composition.

20. A solid cleansing composition which comprises:
(a) at least 15% wt of a non-soap anionic surfactant having a melting point of at least 45° C.;
(b) at least 10% wt of a carrier having a melting point of at least 45° C.;
(c) at least 3% wt of an emulsifier; and
(d) at least 7% wt water;
wherein the composition is a solid throughout the range from 0° C. to 40° C.;
wherein the composition does not contain soap;
wherein the carrier (b) is a triglyceride;
wherein the emulsifier, component (c), has an HLB value of up to 12; and
wherein when two or more emulsifiers are present, the HLB is a weighted average taking into account the individual HLB values and amounts of the two or more emulsifiers.

21. An emulsion for the preparation of a solid cleansing composition, wherein the composition is a solid throughout the range from 0° C. to 40° C., the emulsion comprising:
(a) at least 20% wt and up to 50% wt of a non-soap anionic surfactant having a melting point of at least 45° C.;
(b) at least 20% wt and up to 50% wt of a carrier having a melting point of at least 45° C.;
(c) at least 2% wt and up to 9% wt of an emulsifier; and
(d) at least 16% wt and up to 50 wt % water;
wherein the emulsion does not contain soap;
wherein the emulsion is at a temperature of at least 45° C.;
wherein the emulsifier, component (c), has an HLB value of up to 12;
wherein when two or more emulsifiers are present, the HLB is a weighted average taking into account the individual HLB values and amounts of the two or more emulsifiers; and
wherein components (a) to (d) make up at least 70% and up to 100% of the weight of the emulsion.

22. The method as claimed in claim 1, wherein the solid cleansing composition is in the form of noodles, pellets, flakes or powder.

23. The method as claimed in claim 1, wherein the method comprises a step (iii) of consolidating the solid cleansing composition into a block, bar or tablet.

24. The method as claimed in claim 1, wherein the non-soap anionic surfactant constitutes at least 20% wt and up to 60% wt of the solid cleansing composition.

25. The method as claims in claim 1, wherein the solid cleansing composition comprises:
a. at least 35% wt and up to 55% wt of a non-soap anionic surfactant having a melting point of at least 50° C.;
b. at least 20% wt and up to 40% wt of a triglyceride having a melting point of at least 50° C.;
c. at least 3% wt and up to 8% wt of an emulsifier;
d. at least 8% wt and up to 12% wt of water;
wherein components (a) to (d) make up at least 80% and up to 100% of the weight of the cleansing composition.

26. The solid cleansing composition according to claim 20, wherein the emulsifier, component (c), has an HLB value of at least 6 and up to 12; wherein when two or more emulsifiers are present, the HLB is a weighted average taking into account the individual HLB values and amounts of the two or more emulsifiers.

27. The solid cleansing composition according to claim 20, which comprises:
a. at least 20% wt and up to 60% wt of a non-soap anionic surfactant having a melting point of at least 45° C.;
b. at least 20% wt and up to 60% wt of a triglyceride carrier having a melting point of at least 45° C.;
c. at least 3% wt and up to 9% wt of an emulsifier;
d. at least 5% wt and up to 14% wt of water;
wherein components (a) to (d) make up at least 70% and up to 100% of the weight of the solid cleansing composition;

wherein the composition is a solid throughout the range from 0° C. to 40° C.; and wherein the solid cleansing composition has a completely or predominantly homogeneous microstructure.

28. The solid cleansing composition according to claim 20, wherein the solid cleansing composition is in the form of noodles, pellets, flakes or powder, or has been consolidated into the form of a block, bar or tablet.

\* \* \* \* \*